United States Patent
Py

(10) Patent No.: US 7,905,257 B2
(45) Date of Patent: *Mar. 15, 2011

(54) STERILE FILLING MACHINE HAVING NEEDLE FILLING STATION AND CONVEYOR

(76) Inventor: Daniel Py, Stamford, CT (US)

(*) Notice: Subject to any disclaimer, the term of this patent is extended or adjusted under 35 U.S.C. 154(b) by 0 days.

This patent is subject to a terminal disclaimer.

(21) Appl. No.: 12/496,985

(22) Filed: Jul. 2, 2009

(65) Prior Publication Data

US 2009/0308485 A1 Dec. 17, 2009

Related U.S. Application Data

(63) Continuation of application No. 11/527,775, filed on Sep. 25, 2006, now Pat. No. 7,556,066, which is a continuation of application No. 11/103,803, filed on Apr. 11, 2005, now Pat. No. 7,111,649, which is a continuation of application No. 10/600,525, filed on Jun. 19, 2003, now Pat. No. 6,929,040.

(60) Provisional application No. 60/390,212, filed on Jun. 19, 2002.

(51) Int. Cl.
*B65B 1/20* (2006.01)
*B65B 55/14* (2006.01)

(52) U.S. Cl. ............ 141/11; 141/69; 141/85; 141/130; 141/329; 53/426; 53/440; 53/127

(58) Field of Classification Search ............... 141/2, 11, 141/18, 69, 83, 85, 94, 129, 130, 329, 330; 604/256, 414, 415, 537; 53/425, 426, 428, 53/440, 111 R, 127

See application file for complete search history.

(56) References Cited

U.S. PATENT DOCUMENTS

| | | | |
|---|---|---|---|
| 2,667,986 | A | 2/1954 | Perelson |
| 3,136,440 | A | 6/1964 | Krug et al. |
| 3,278,063 | A | 10/1966 | Kranzhoff |
| 3,392,859 | A | 7/1968 | Fischer |
| 3,780,308 | A | 12/1973 | Nablo |
| 3,811,591 | A | 5/1974 | Novitch |
| 4,048,255 | A | 9/1977 | Hillier et al. |
| 4,390,111 | A | 6/1983 | Robbins et al. |
| 4,444,330 | A | 4/1984 | Kasai et al. |
| 4,499,148 | A | 2/1985 | Goodale et al. |
| 4,652,763 | A | 3/1987 | Nablo |
| 4,815,619 | A | 3/1989 | Turner et al. |

(Continued)

FOREIGN PATENT DOCUMENTS

CA 1 123 792 5/1982

(Continued)

*Primary Examiner* — Timothy L Maust
(74) *Attorney, Agent, or Firm* — McCarter & English, LLP

(57) ABSTRACT

A sterile filling machine and related method are provided for sterile filling a container with a substance. The container includes a heat resealable stopper and a chamber for receiving the substance therein. The sealed, empty containers are subjected to radiation capable of penetrating through the stopper and chamber for sterilizing the container. The previously sterilized containers are then transported through another sterilizing chamber, such as an e-beam chamber, to sterilize the penetrable surface. A needle is moved into engagement with the stopper to pierce the sterilized penetrable surface of the stopper and inject the substance through the needle and into the chamber of the container. Laser energy is then transmitted onto the penetrated surface of the stopper to fuse the stopper material and hermetically re-seal the stopper.

22 Claims, 1 Drawing Sheet

U.S. PATENT DOCUMENTS

| | | |
|---|---|---|
| 4,834,152 A | 5/1989 | Howson et al. |
| 4,910,435 A | 3/1990 | Wakalopulos |
| 5,009,654 A | 4/1991 | Minshall et al. |
| 5,031,675 A | 7/1991 | Lindgren |
| 5,088,995 A | 2/1992 | Packard et al. |
| 5,129,212 A | 7/1992 | Duffey et al. |
| 5,414,267 A | 5/1995 | Wakalopulos |
| 5,484,566 A | 1/1996 | Gabbard |
| 5,496,302 A | 3/1996 | Minshall et al. |
| RE35,203 E | 4/1996 | Wakalopulos |
| 5,612,588 A | 3/1997 | Wakalopulos |
| 5,641,004 A | 6/1997 | Py |
| 5,702,019 A | 12/1997 | Grimard |
| 5,909,032 A | 6/1999 | Wakalopulos |
| 5,971,181 A | 10/1999 | Niedospial, Jr. et al. |
| 6,050,435 A | 4/2000 | Bush et al. |
| 6,140,657 A | 10/2000 | Wakalopulos et al. |
| 6,168,037 B1 | 1/2001 | Grimard |
| 6,364,864 B1 | 4/2002 | Mohiuddin et al. |
| 6,382,441 B1 | 5/2002 | Carano |
| 6,604,561 B2 | 8/2003 | Py |
| 6,929,040 B2 | 8/2005 | Py |
| 7,111,649 B2 | 9/2006 | Py |
| 7,556,066 B2 * | 7/2009 | Py ................... 141/85 |
| 7,726,357 B2 * | 6/2010 | Py et al. .............. 141/69 |
| 2001/0041872 A1 | 11/2001 | Paul, Jr. |
| 2002/0006353 A1 | 1/2002 | Bilstad et al. |
| 2002/0010995 A1 | 1/2002 | Thibault et al. |
| 2002/0018731 A1 | 2/2002 | Bilstad et al. |
| 2002/0023409 A1 | 2/2002 | Py |
| 2002/0029022 A1 | 3/2002 | Naritomi et al. |
| 2002/0069616 A1 | 6/2002 | Odell et al. |
| 2002/0131902 A1 | 9/2002 | Levy |
| 2002/0172615 A1 | 11/2002 | Woodworth et al. |
| 2003/0156973 A1 | 8/2003 | Bilstad et al. |

FOREIGN PATENT DOCUMENTS

| | | |
|---|---|---|
| GB | 984149 | 2/1965 |
| GB | 2 364 700 | 2/2002 |
| JP | 52-017469 | 5/1977 |
| JP | 10-045116 | 2/1998 |
| JP | 2002-104334 | 4/2002 |
| JP | 2002-173114 | 6/2002 |

* cited by examiner

STERILE FILLING MACHINE HAVING NEEDLE FILLING STATION AND CONVEYOR

CROSS-REFERENCE TO RELATED APPLICATION

This patent application is a continuation of U.S. application Ser. No. 11/527,775, filed Sep. 25, 2006 now U.S. Pat. No. 7,556,066, which is a continuation of U.S. application Ser. No. 11/103,803, filed Apr. 11, 2005, now U.S. Pat. No. 7,111,649, which is a continuation of U.S. application Ser. No. 10/600,525, filed Jun. 19, 2003, now U.S. Pat. No. 6,929,040, which claims priority to U.S. Provisional Application Ser. No. 60/390,212, filed Jun. 19, 2002, the contents of which are hereby expressly incorporated by reference in their entireties as part of the present disclosure.

FIELD OF THE INVENTION

The present invention relates to apparatus and methods for filling medicaments or other substances into containers, and more particularly, to apparatus and methods for sterile filling medicaments or other substances into hermetically sealed containers, such as vials or syringes.

BACKGROUND INFORMATION

A typical medicament dispenser includes a body defining a storage chamber, a fill opening in fluid communication with the body, and a stopper or cap for sealing the fill opening after filling the storage chamber to hermetically seal the medicament within the dispenser. In order to fill such prior art dispensers with a sterile fluid or other substance, such as a medicament, it is typically necessary to sterilize the unassembled components of the dispenser, such as by autoclaving the components and/or exposing the components to gamma radiation. The sterilized components then must be filled and assembled in an aseptic isolator of a sterile filling machine. In some cases, the sterilized components are contained within multiple sealed bags or other sterile enclosures for transportation to the sterile filling machine. In other cases, the sterilization equipment is located within the isolator of the sterile filling machine. In the isolator, the storage chamber is filled with the fluid or other substance, and then the sterilized stopper is assembled to the dispenser to plug the fill opening and hermetically seal the fluid or other substance in the dispenser.

One of the drawbacks of such prior art dispensers, and processes and equipment for filling such dispensers, is that the filling process is time consuming, and the processes and equipment are expensive. Further, the relatively complex nature of the filling processes and equipment can lead to more defectively filled dispensers than otherwise desired.

The present inventor has recognized the advantages of sterilizing a sealed, empty dispenser, and then filling the sterilized, sealed, empty dispenser under a laminar flow to maintain aseptic conditions during filling. For example, co-pending U.S. patent application Ser. No. 09/781,846, filed Nov. 25, 2002, entitled "Medicament Vial Having a Heat-Sealable Cap, and Apparatus and Method for Filling the Vial", and U.S. Provisional Application Ser. No. 60/442,526, filed Jan. 28, 2003, entitled "Medicament Vial Having A Heat-Sealable Cap, And Apparatus And Method For Filling The Vial", each of which is assigned to the Assignee of the present invention and is hereby expressly incorporated by reference as part of the present disclosure, disclose a vial including a resealable stopper. The resealable stopper is first sealed to the empty vial, and then the empty vial/stopper assembly is sterilized, such as by applying gamma radiation thereto. The sterilized, sealed, empty vial/stopper assembly is then filled by piercing the resealable stopper with a needle, and introducing the fluid or other substance through the needle and into the chamber of the vial. Then, the needle is withdrawn, and laser radiation is transmitted onto the penetrated region of the stopper to seal the needle hole and hermetically seal the sterile fluid or other substance within the vial/stopper assembly.

Although this resealable stopper, apparatus and method overcome many of the drawbacks and disadvantages associated with prior art equipment and processes for sterile filling, in certain applications it may be desirable to further avoid the possibility of contaminating the container between sterilization and filling of the container.

Accordingly, it is an object of the currently preferred embodiments of the present invention to overcome one or more of the above-described drawbacks and/or disadvantages and to provide an apparatus and method for needle filling a container including a resealable stopper in an e-beam chamber.

SUMMARY OF THE INVENTION

The present invention is directed to an apparatus for sterile filling a container with a substance, wherein the container includes a heat resealable stopper and a chamber for receiving the substance therein. In one embodiment of the present invention, the apparatus comprises an e-beam chamber for receiving the container therein; and an e-beam source for directing an electron beam within the e-beam chamber onto a penetrable surface of the stopper to sterilize the penetrable surface. A filling member, such as a needle, may be mounted within the e-beam chamber and is movable into and out of engagement with the resealable stopper for piercing the resealable stopper and introducing a substance through the stopper and into the sealed chamber of the container. In one embodiment, the e-beam source and the needle are located within the e-beam chamber and are positioned relative to each other to cause e-beam radiation from the e-beam source to impinge on the needle and maintain needle sterility during filling of a plurality of containers. An energy source, such as a laser, is connectable in thermal communication with the penetrable surface of the resealable stopper for applying energy to the penetrable surface after withdrawing the needle therefrom to hermetically seal the penetrated surface.

In one embodiment of the present invention, the apparatus further comprises a radiation source, such as a gamma source, located external to the e-beam chamber, for generating radiation capable of penetrating through the stopper and chamber of the container and sterilizing the container prior to transporting the container through the e-beam chamber.

In one embodiment of the present invention, the apparatus further comprises a conveyor extending within the e-beam chamber, a motor drivingly coupled to the conveyor for moving the conveyor and, in turn, transporting the container on the conveyor through the e-beam chamber, and a control unit coupled to the e-beam source and the motor. The control unit controls at least one of the current, scan width, and energy of the e-beam source and the speed of the conveyor to achieve at least about a 3 log reduction, and preferably at least about a 6 log reduction, in bio-burden on the penetrable surface of the stopper.

In one embodiment of the present invention, the apparatus comprises a laser source for transmitting laser radiation at a predetermined wavelength and power, and a container including a heat resealable stopper and a chamber for receiving the substance therein. The resealable stopper includes a thermoplastic body defining (i) a predetermined wall thickness in an axial direction thereof, (ii) a predetermined color and opacity that substantially absorbs the laser radiation at the predetermined wavelength and substantially prevents the passage of the radiation through the predetermined wall thickness thereof, and (iii) a predetermined color and opacity that causes the laser radiation at the predetermined wavelength and power to hermetically seal a needle aperture formed in the needle penetration region thereof in a predetermined time period.

The present invention also is directed to a method for sterile filling a container with a substance, wherein the container includes a heat resealable stopper and a chamber for receiving the substance therein. In one embodiment, the method comprises the steps of:

(i) sealing the stopper to the container;

(ii) transporting the sealed, empty containers through an e-beam chamber;

(iii) directing an electron beam within the e-beam chamber onto a penetrable surface of the stopper to sterilize the penetrable surface;

(iv) introducing a needle within the e-beam chamber through the sterilized penetrable surface of the stopper;

(v) introducing through the needle a substance into the chamber of the container;

(vi) withdrawing the needle from the stopper upon introducing the substance through the needle and into the chamber;

(vii) transporting the filled containers out of the e-beam chamber; and (viii) applying energy to the penetrated surface of the stopper and hermetically sealing same.

In one embodiment of the present invention, the method further comprises the step of subjecting the sealed, empty container to radiation, such as gamma radiation, that is capable of penetrating through the stopper and chamber and sterilizing the container, prior to transporting the container through the e-beam chamber.

One advantage of the illustrated embodiment of the apparatus and method of the present invention is that it substantially eliminates any risk of contaminating the containers between sterilization and filling because the needle or like filling member is located within the e-beam chamber.

Other advantages of the present invention will become more readily apparent in view of the following detailed description of the currently preferred embodiment and the accompanying drawing.

DETAILED DESCRIPTION OF THE PREFERRED EMBODIMENT

Figure 1:
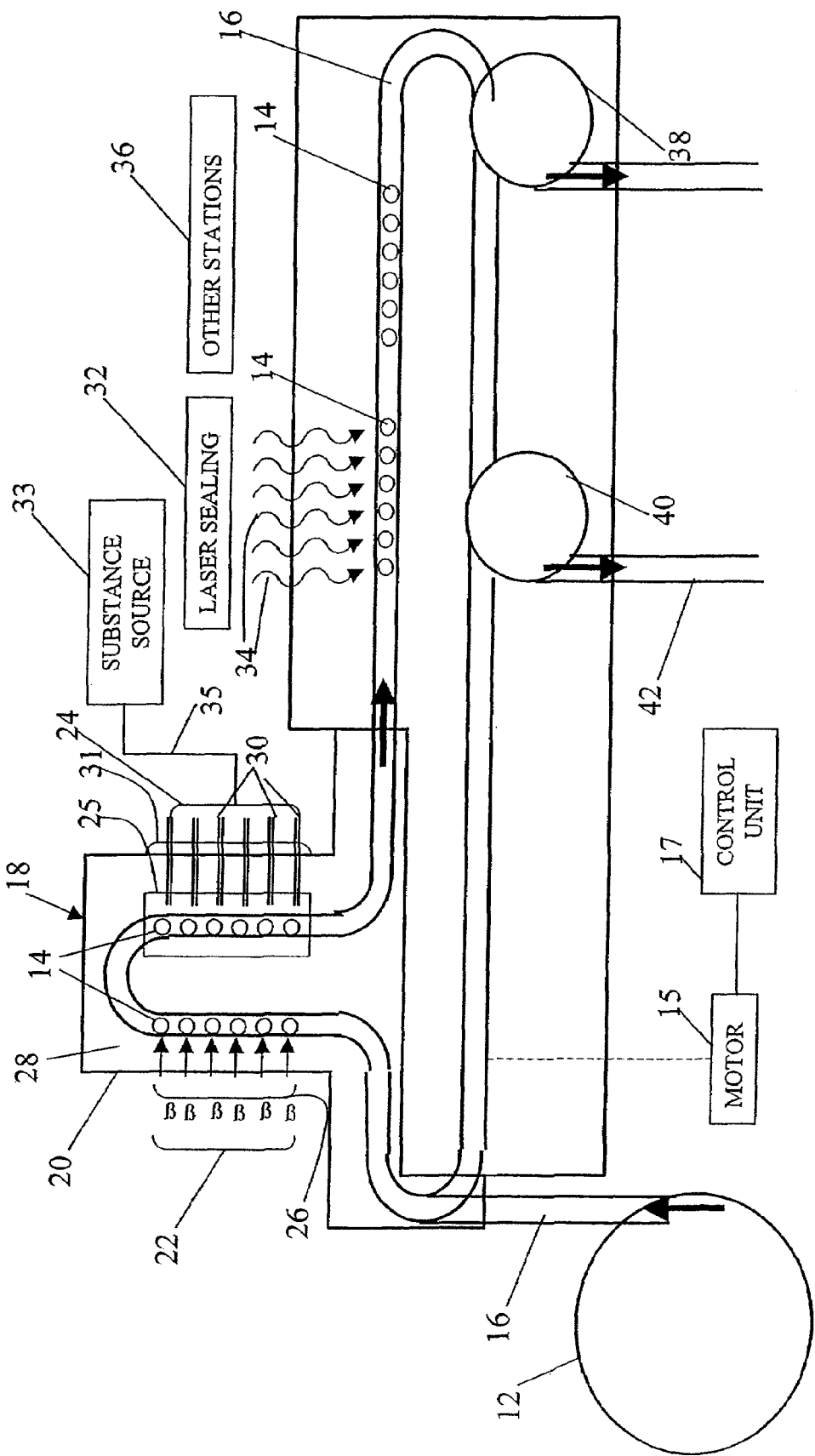
FIG. 1 is a somewhat schematic plan view of a sterile filling machine embodying the present invention.

In FIG. 1, a sterile filling machine ("SFM") embodying the present invention is indicated generally by the reference numeral 10. In the currently preferred embodiment of the invention, the SFM 10 is used to fill vials or syringes for containing medicaments, such as vaccines or pharmaceutical products. However, as may be recognized by those of ordinary skill in the pertinent art based on the teachings herein, the SFM 10 equally may be used for filling any of numerous other types of containers or delivery devices with the same or other substances, such as cosmetics and food products. The SFM 10 comprises an infeed unit 12 for holding the vials, syringes or other containers 14 to be delivered into the SFM. In the illustrated embodiment of the present invention, the infeed unit 12 is in the form of a rotary table that holds a plurality of vials, syringes or other containers 14, and delivers the containers at a predetermined rate into the SFM. As may be recognized by those of ordinary skill in the pertinent art based on the teachings herein, the infeed unit 12 may take the form of any of numerous devices that are currently, or later become known for performing the function of the infeed unit 12, such as any of numerous different types of vibratory feed drives, or "pick and place" robotic systems.

Prior to installing the vials or other containers 14 on the infeed unit 12, the sealed containers (e.g., the empty vials with the stoppers sealed thereto) are preferably sterilized, such as by exposing the containers to gamma radiation, in a manner known to those of ordinary skill in the pertinent art. In addition, the vial assemblies or other sealed, empty containers, may be enclosed, sterilized, and transported to the SFM 10 in accordance with the teachings of U.S. Pat. No. 5,186,772, entitled "Method of Transferring Articles, Transfer Pocket And Enclosure", and U.S. patent application Ser. No. 10/241,249, filed Sep. 10, 2002, entitled "Transfer Port and Method for Transferring Sterile Items", each of which is assigned to the Assignee of the present invention and is hereby expressly incorporated by reference as part of the present disclosure. Once loaded onto the SFM 10, the vials or other containers 14 are sterilized again by e-beam radiation in order to further ensure absolute sterility of the requisite surfaces prior to filling and sealing, as described further below.

A conveyor 16 is coupled to the infeed unit 12 for receiving the vials or other containers 14 delivered by the infeed unit and for transporting the vials or other containers at a predetermined rate through the SFM 10 in the directions indicated by the arrows in FIG. 1. In the illustrated embodiment of the present invention, the conveyor 16 preferably transports the containers 14 in a single file relative to each other. In the event the containers 14 are vials, each vial preferably defines a substantially "diabolo" shape formed by a base, a cap and a body extending between the base and cap, wherein the base and cap define a diameter or width that is greater than that of the body. The diabolo shape may facilitate securing and otherwise transporting the vials through the SFM 10. Vials of this type are disclosed in co-pending U.S. Provisional Patent Application Ser. No. 60/408,068, filed Sep. 3, 2002, entitled "Sealed Containers and Methods of Making and Filling Same", and U.S. patent application Ser. No. 29/166,810, filed Sep. 3, 2002, entitled "Vial", each of which is assigned to the Assignee of the present invention and is hereby expressly incorporated by reference as part of the present disclosure.

The conveyor 16 may take the form of any of numerous different types of conveyers that are currently, or later become known, for performing the functions of the conveyor described herein. For example, the conveyor may take the form of a vibratory feed drive, or may take the form of an endless conveyor belt including, for example, a plurality of receptacles, such as cleats, for receiving or otherwise holding the vials or other containers 14 at predetermined positions on the conveyor. The conveyor 16 is drivingly connected to a motor or other suitable drive source 15, which is controlled by a computer or other control unit 17 to start, stop, control the speed, and otherwise coordinate operation of the conveyor with the other components of the SFM.

The SFM 10 further includes an e-beam and needle filling assembly 18 comprising an e-beam housing 20, at least one e-beam source 22, and a needle filling station 24 mounted within the e-beam housing. The e-beam source 22 may be any of numerous different types of e-beam sources that are currently, or later become known, for performing the function of the e-beam source 22 described herein. E-beam radiation is a form of ionizing energy that is generally characterized by its low penetration and high dose rates. The electrons alter various chemical and molecular bonds upon contact with an exposed product, including the reproductive cells of microorganisms, and therefore e-beam radiation is particularly suitable for sterilizing vials, syringes and other containers for medicaments or other sterile substances. As indicated by the arrows in FIG. 1, the e-beam source 22 produces an electron beam 26 that is formed by a concentrated, highly charged stream of electrons generated by the acceleration and conversion of electricity. Preferably, the electron beam 26 is focused onto a penetrable surface of each container 14 for piercing by a needle to thereby fill the container with a medicament or other substance. For example, in the case of vials, such as the vials including resealable stoppers as described, for example, in the above-mentioned co-pending patent applications, the electron beam 26 is focused onto the upper surface of the stopper to sterilize the penetrable surface of the stopper prior to insertion of the filling needle therethrough. In addition, reflective surfaces may be mounted on opposite sides of the conveyor relative to each other, or otherwise in a manner known to those of ordinary skill in the pertinent art based on the teachings herein, to reflect the e-beam, and/or the reflected and scattered electrons of the e-beam, onto the sides of the vials or other containers 14 to sterilize these surfaces as well. Alternatively, or in combination with such reflective surfaces, more than one e-beam source 22 may be employed, wherein each e-beam source is focused onto a respective surface or surface portion of the vials or other containers 14 to ensure sterilization of each surface or surface area of interest.

The e-beam housing 20 is constructed in a manner known to those of ordinary skill in the pertinent art based on the teachings herein to define an e-beam chamber 28 and means for preventing leakage of the electrons out of the chamber in accordance with applicable safety standards. As shown in FIG. 1, the conveyor 16 defines an approximately U-shaped path within the e-beam chamber 28, wherein the first leg of the U defines an inlet section and the portion of the chamber onto which the e-beam 26 is directed. In the currently preferred embodiment of the present invention, the current, scan width, position and energy of the e-beam 26, the speed of the conveyor 16, and/or the orientation and position of any reflective surfaces, are selected to achieve at least about a 3 log reduction, and preferably at least about a 6 log reduction in bio-burden testing on the upper surface of the vial's or other container's resealable stopper, i.e., the surface of the stopper defining the penetrable region that is pierced by a filling needle to fill the vial. In addition, as an added measure of caution, one or more of the foregoing variables also are preferably selected to achieve at least about a 3 log reduction on the sides of the vial or other container, i.e., on the surfaces of the vial that are not pierced by the needle during filling. These specific levels of sterility are only exemplary, however, and the sterility levels may be set as desired or otherwise required to validate a particular product under, for example, United States FDA or applicable European standards, such as the applicable Sterility Assurance Levels ("SAL").

The e-beam and needle filling assembly 18 also preferably includes means 25 for visually inspecting the filling station 24. This means may take the form of a beta-barrier window (i.e., a window that blocks any e-beam radiation but permits visual inspection therethrough), and/or a CCD, video or other camera mounted within the housing for transmitting to an external monitor (not shown) images of the filling station 24. As may be recognized by those of ordinary skill in the pertinent art based on the teachings herein, these particular devices are only exemplary, and any of numerous other devices that are currently, or later become known, for performing the function of permitting visual inspection equally may be employed.

As shown in FIG. 1, the needle filling station 24 is mounted on the opposite leg, or outlet side of the U-shaped conveyor path within the e-beam chamber 28. In the illustrated embodiment of the present invention, the needle station 24 includes a plurality of needles 30 or other filling members mounted over the conveyor 16, wherein each needle is drivingly mounted over the conveyor in the same manner as described, for example, in the above-mentioned co-pending patent applications. Accordingly, each needle 30 is movable into and out of engagement with the resealable stoppers to pierce the stoppers and fill the vials or other containers 14 with a medicament or other substance to be contained therein, and to then withdraw the needle upon filling the vial or other container. In the illustrated embodiment, the needle filling station 24 includes a bank of six needles 30 mounted in line with each other and overlying the conveyor 16 to allow the simultaneous piercing and in-line filling of six vials or other containers. The needles 30 may be mounted on a common drive unit, or each needle may be individually actuatable into and out of engagement with the resealable stoppers of the vials or other containers 14. As may be recognized by those of ordinary skill in the pertinent art based on the teachings herein, the needle filling station 24 may include any desired number of needles 30, or may be mounted or driven in any of numerous different ways that are currently, or later become known, for performing the functions of the needle filling station described herein. Similarly, the SFM 10 may include a plurality of needle filling stations 24 mounted within the same e-beam chamber 28, or a plurality of e-beam and needle filling assemblies, in order to increase or otherwise adjust the overall throughput of the SFM 10. Preferably, the e-beam housing 20 defines a port 31 or other removable passageway to allow access to and/or repair and replacement of the needle filling station 24. Each needle 30 is connected in fluid communication to a substance source 33 by one or more filling lines 35 for receiving therefrom a medicament of other substance to be filled into the vials or other containers 14. The substance source 33 is preferably mounted external to the e-beam chamber 28, and the filling line(s) 35 connected between the substance source 33 and needles 30 are protected by suitable shielding, an electron trap, and/or other arrangement that is currently, or later becomes known to those of ordinary skill in the pertinent art, to prevent radiation within the e-beam chamber 28 from degrading or otherwise damaging the substance flowing through the line(s) 35 from the substance source 31 to the needles 30.

As can be seen in FIG. 1, the e-beam and needle filling assembly 18 is configured so that the needles 30 of the needle filling station are mounted within the e-beam chamber 28. As a result, the free electrons within the e-beam chamber will impinge upon the needles 30. This, in combination with operation of the e-beam 26 which sterilizes the air throughout the e-beam chamber, functions to sterilize the needles and/or maintain the sterility of the needles throughout the filling process. Preferably, the current, scan width, relative position and energy of the e-beam 26, and/or the orientation and position of any reflective surfaces, are selected to achieve at least about a 3 log reduction, and preferably at least about a 6 log reduction in bio-burden testing on the external surfaces of the needles 30, including but not necessarily limited to, the surfaces of the needles that contact the resealable stoppers of the vials or other containers 14. Further, these levels of sterility are achievable within the shadows of the needles 30 relative to the e-beam source 22 due to the electronic cloud of e-beam radiation formed within and around the needles. These specific levels of sterility are only exemplary, however, and the sterility levels may be set as desired or otherwise required to validate a particular product under, for example, United States FDA or applicable European standards, such as the applicable SAL.

Since the containers or other vials are filled within the e-beam chamber 28, there is virtually no risk that the containers will become contaminated between e-beam sterilization and filling. If desired, the air within the e-beam chamber may be ionized to promote multiplication of the free electrons and further enhance the sterility of the filling station. Another advantage of the SFM of the present invention is that a laminar flow of air over the needles during filling may be unnecessary to achieve the requisite level of sterility. In addition, this feature of the present invention may further obviate the need for a laminar flow of air over the resealable stoppers during laser or other thermal sealing of the stoppers. In the illustrated embodiment of the present invention, there may be little, if any, concern that the filled vials or other containers will become contaminated during the brief period of transportation between the needle filling and laser sealing stations. Furthermore, this feature of the invention obviates any need for an isolator, as found in many prior art sterile filling machines.

The SFM 10 further includes a laser sealing station 32 mounted over the conveyor 16 immediately downstream the outlet of the e-beam and needle filling assembly 18. In the illustrated embodiment of the invention, the laser sealing station 32 preferably includes a plurality of lasers, each mounted over a respective vial or other container 14 for transmitting a respective laser beam 34 onto the vial to heat seal the needle aperture in the resealable stopper. In the illustrated embodiment of the present invention, each laser is a diode laser fiber-optically coupled to a respective outlet port overlying the conveyor and focused onto a respective stopper position on the conveyor. For example, the lasers may take the form of the fiber coupled diode laser units manufactured by Semiconductor Laser International Corp. of Binghamton, N.Y., USA. A significant advantage of this type of laser system is that the lasers may be mounted remote from the laser sealing station 32 and mounted, for example, outside of any enclosure for the laser sealing station. As a result, any laser repair or replacement may be performed outside of the laser sealing or other enclosure facilitating a significantly less expensive and time consuming procedure than if the laser were mounted within the enclosure. The laser sealing station 32 also preferably includes a smoke removal unit of a type known to those of ordinary skill in the pertinent art for removing any smoke, vapors or gases generated upon heat sealing the stoppers. As may be recognized by those of ordinary skill in the pertinent art based on the teachings herein, other types of laser, radiation, or other energy sources that are currently or later become known equally may be used to heat seal the penetrated regions of the stoppers.

In the illustrated embodiment of the invention, each resealable stopper is formed of a thermoplastic material defining a needle penetration region that is pierceable with a needle to form a needle aperture therethrough, and is heat resealable to hermetically seal the needle aperture by applying laser radiation at a predetermined wavelength and power thereto. Each stopper comprises a thermoplastic body defining (i) a predetermined wall thickness in an axial direction thereof, (ii) a predetermined color and opacity that substantially absorbs the laser radiation at the predetermined wavelength and substantially prevents the passage of the radiation through the predetermined wall thickness thereof, and (iii) a predetermined color and opacity that causes the laser radiation at the predetermined wavelength and power to hermetically seal the needle aperture formed in the needle penetration region thereof in a predetermined time period and substantially without burning the needle penetration region (i.e., without creating an irreversible change in molecular structure or chemical properties of the material). In a currently preferred embodiment, the predetermined time period is approximately 2 seconds, and is most preferably less than or equal to about 1.5 seconds. Also in a currently preferred embodiment, the predetermined wavelength of the laser radiation is about 980 nm, and the predetermined power of each laser is preferably less than about 30 Watts, and most preferably less than or equal to about 10 Watts, or within the range of about 8 to about 10 Watts. Also in the currently preferred embodiment, the predetermined color of the material is gray, and the predetermined opacity is defined by a dark gray colorant added to the stopper material in an amount within the range of about 0.3% to about 0.6% by weight. In addition, the thermoplastic material may be a blend of a first material that is preferably a styrene block copolymer, such as the materials sold under either the trademarks KRATON or DYNAFLEX, and a second material that is preferably an olefin, such as the materials sold under either the trademarks ENGAGE or EXACT. In one embodiment of the invention, the first and second materials are blended within the range of about 50:50 by weight to about 90:10 by weight (i.e., first material:second material). In one embodiment of the invention, the blend of first and second materials is about 50:50 by weight. The benefits of the preferred blend over the first material by itself are improved water or vapor barrier properties, and thus improved product shelf life; improved heat sealability; a reduced coefficient of friction; improved moldability or mold flow rates; and a reduction in hystereses losses. Further, if desired, the material may include a medical grade silicone or other suitable lubricant to facilitate preventing the formation of particles upon penetrating the resealable stoppers with the needles. As may be recognized by those skilled in the pertinent art, however, these numbers and materials are only exemplary, and may be changed if desired or otherwise required in a particular system.

As shown in FIG. 1, the SFM 10 includes one or more other stations 36 located downstream of the laser sealing station 32. The other stations 36 may include a vision system of a type known to those of ordinary skill in the pertinent art for inspecting each laser or other seal, a level detection system for detecting the level of fluid or other substance within each vial or other container 14 to ensure that it is filled to the correct level, and a labeling station. In addition, as shown in FIG. 1, the SFM 10 includes a rejection unit 38 for pulling off of the conveyer any vials or other containers 14 that are defective as detected, for example, by the laser or other seal inspection, level detection inspection, or due to mislabeling or defective labeling. Then, the acceptable vials or other containers are removed by a discharge unit 40 for discharging the vials or other containers into a collection unit 42 for packing and shipping. The rejection and discharge units may take the forms of star wheels, pick and place robots, or any of numerous other devices that are currently or later become known for performing the functions of these units described herein.

A significant advantage of the present invention is that it enables true sterile filling and not only aseptic filling. Another advantage of the illustrated embodiment of the present invention is that the medicament or other substance is filled after subjecting the containers to gamma and direct e-beam radiation, thus preventing the radiation from degrading the medicament or other substance to be contained within the container. Yet another advantage of the present invention is that there is substantially zero possibility of contaminating the vials or other containers between the sterilization and filling steps.

As may be recognized by those of ordinary skill in the pertinent art based on the teachings herein, numerous changes and modifications may be made to the above-described and other embodiments of the invention without departing from its scope as defined in the claims. For example, the form and configuration of many of the components of the SFM disclosed herein may change, or any number of stations may be added to the SFM to provide additional functionality. In addition, the containers may take the form of any of numerous different vials, syringes or other containers. Accordingly, this detailed description of preferred embodiments is to be taken in an illustrative as opposed to a limiting sense.

What is claimed is:

1. A method comprising the following steps:
providing a plurality of devices, wherein each device includes a penetrable and resealable portion, and a sealed empty chamber in fluid communication with the penetrable and resealable portion;
sterilizing the plurality of sealed, empty devices by subjecting them to radiation capable of penetrating through the penetrable and resealable portions and into the chambers;
transporting the plurality of devices with sterilized internal chambers on a conveyor;
conveying the devices through a sterilizing station and sterilizing at least an external surface of the penetrable and resealable portions of the devices;
introducing at least one injection member through the penetrable and resealable portions of the devices;
introducing through the at least one injection member a sterile substance into the sterile chambers of the devices;
withdrawing the at least one injection member from the penetrable and resealable portions; and
resealing the penetrable and resealable portions and sealing the sterile substance within the devices.

2. A method as defined in claim 1, further comprising moving the conveyor by motor and holding the devices in predetermined positions thereon.

3. A method as defined in claim 1, further comprising introducing through the at least one injection member one of a sterile medicament, cosmetic and food product.

4. A method as defined in claim 1, wherein the resealing step includes transmitting laser radiation onto the penetrated surfaces of the penetrable and resealable portions of the devices.

5. A method as defined in claim 4, further comprising transporting the devices on the conveyor from the sterilizing station to a filling station including therein the at least one injection member, and transporting the devices on the conveyor from the filling station to a laser resealing station and transmitting within the laser resealing station the radiation onto the penetrated surfaces and thermally resealing same.

6. A method as defined in claim 1, wherein the step of sterilizing the devices by subjecting them to radiation includes subjecting the devices to gamma radiation, and the step of conveying the devices through a sterilizing station and sterilizing at least the external surfaces of the penetrable and resealable portions includes directing an electron beam onto such surfaces.

7. A method as defined in claim 1, further comprising drivingly mounting a plurality of needles over the conveyor, driving the plurality of needles into engagement with a plurality of penetrable and resealable portions and piercing such portions, and introducing the substance through the needles and into the chambers of the devices.

8. A method as defined in claim 4, further comprising providing a penetrable and resealable portion having a needle penetration region defining a predetermined color and opacity that causes laser radiation at a predetermined wavelength and power to hermetically seal a needle aperture formed in the needle penetration region thereof in a predetermined time period of less than or equal to about 2 seconds.

9. A system for sterile filling devices with a substance, wherein each device includes a penetrable and resealable portion and a chamber for receiving the substance therein, comprising:
a radiation source for generating radiation capable of penetrating the chambers of the devices and sterilizing the devices;
a motorized conveyor that holds the devices with sterilized internal chambers in predetermined positions thereon and transports the devices along a conveyor path;
a sterilizing source located adjacent to the conveyor path that sterilizes at least an external surface of the penetrable and resealable portions of the devices;
a plurality of injection members movably mounted relative to the conveyor path, wherein each injection member is movable into and out of engagement with the penetrable and resealable portion of a respective device and is configured to pierce such portion and introduce a substance therethrough and into the sealed chamber of the device; and
a device for hermetically sealing resulting penetration holes formed by the injection members.

10. A system as defined in claim 9, wherein the radiation source is a gamma radiation source, and the sterilizing source is an e-beam source that directs an e-beam onto an external surface of the penetrable and resealable portions of the devices to sterilize the irradiated surfaces.

11. A system as defined in claim 9, wherein the device for hermetically sealing resulting penetration holes is a radiation source configured to transmit radiation at a predetermined wavelength and power onto the penetrated surfaces of the devices.

12. A system as defined in claim 11, further comprising a plurality of devices, wherein each device includes a penetrable and resealable portion and a chamber for receiving the substance therein, and the penetrable and resealable portion includes a penetration region that defines a predetermined color and opacity that substantially absorbs laser radiation at the predetermined wavelength and power and substantially prevents the passage of such laser radiation through a predetermined wall thickness thereof.

13. A system as defined in claim 12, wherein each penetrable and resealable portion includes a thermoplastic body defining (i) a predetermined wall thickness in an axial direction thereof, (ii) a predetermined color and opacity that substantially absorbs the laser radiation at the predetermined wavelength and substantially prevents the passage of the radiation through the predetermined wall thickness thereof, and (iii) a predetermined color and opacity that causes the laser radiation at the predetermined wavelength and power to hermetically seal a needle aperture formed in the needle penetration region thereof in a predetermined time period.

14. A system as defined in claim 9, further comprising a plurality of devices, wherein each device defines a base, a cap, and a body extending between the base and cap, wherein each of the base and cap defines a diameter or width that is greater than that of the body.

15. A system as defined in claim 9, wherein the conveyor includes a plurality of receptacles for receiving or otherwise holding the devices in predetermined positions on the conveyor.

16. A system as defined in claim 9, further comprising a plurality of injection members mounted over the conveyor that substantially simultaneously pierce and fill a plurality of devices.

17. A method comprising the following steps:
provide a plurality of devices, wherein each device includes a penetrable and resealable portion, and a sealed, empty, sterile chamber in fluid communication with the penetrable and resealable portion;
sterilizing the plurality of sealed, empty devices;
holding the devices at predetermined positions on a conveyor;
driving the conveyor and transporting the devices held at predetermined positions on the conveyor;
sterilizing at least an external surface of the penetrable and resealable portions of the devices on the conveyor;
introducing at least one injection member through the penetrable and resealable portions of the devices held at predetermined positions on the conveyor;
introducing through the at least one injection member a sterile substance into the sterile chambers of the devices;
withdrawing the at least one injection member from the penetrable and resealable portions of the devices held at predetermined positions on the conveyor; and
resealing the penetrable and resealable portions and sealing the sterile substance within the devices.

18. A method as defined in claim 17, wherein the sterilizing step includes sterilizing the plurality of sealed, empty devices by subjecting them to radiation capable of penetrating through the penetrable and resealable portions and into the chambers.

19. A method as defined in claim 17, further comprising introducing through the at least one injection member and into the sterile chambers one of a sterile medicament, cosmetic and food product.

20. A method as defined in claim 17, further comprising holding the devices at predetermined positions on the conveyor with a plurality of receptacles or cleats.

21. A method as defined in claim 17, further comprising driving the conveyor with a drive source drivingly connected to the conveyor, and controlling the drive source with a control unit to start, stop and control the speed of the conveyor.

22. A method as defined in claim 17, wherein the resealing step includes transmitting radiation onto the penetrated surfaces of the penetrable and resealable portions of the devices.

* * * * *